United States Patent [19]
Takeda et al.

[11] Patent Number: 6,146,844
[45] Date of Patent: Nov. 14, 2000

[54] PROCESS FOR PRODUCING HYDROXYLATED CHOLESTEROLS AND DIHYDROXYCHOLESTEROLS USING AMYCOLATA

[75] Inventors: Koji Takeda, Iwata; Tadashi Terasawa, Yatsushiro; Kazuyuki Dobashi, Hadano; Takeo Yoshioka, Ayase, all of Japan

[73] Assignee: Mercian Corporation, Tokyo, Japan

[21] Appl. No.: 09/029,160

[22] PCT Filed: Aug. 26, 1996

[86] PCT No.: PCT/JP96/02369

§ 371 Date: Feb. 26, 1998

§ 102(e) Date: Feb. 26, 1998

[87] PCT Pub. No.: WO97/08336

PCT Pub. Date: Mar. 6, 1997

[30] Foreign Application Priority Data

Aug. 28, 1995 [JP] Japan ..................................... 7-240461
Nov. 15, 1995 [JP] Japan ..................................... 7-319758
Nov. 16, 1995 [JP] Japan ..................................... 7-321250

[51] Int. Cl.[7] ................................................. C12P 33/00
[52] U.S. Cl. .......................................... 435/52; 435/252.1
[58] Field of Search ..................................... 435/52, 252.1

[56] References Cited

U.S. PATENT DOCUMENTS 4,204,995  5/1980  Barner et al. ....................... 260/239.55

FOREIGN PATENT DOCUMENTS

| 0004098 | 9/1979 | European Pat. Off. . |
| 0653490 | 5/1995 | European Pat. Off. . |
| 4-166090 | 6/1992 | Japan . |
| 4-356190 | 12/1992 | Japan . |
| 7-123997 | 5/1995 | Japan . |
| 7-241197 | 9/1995 | Japan . |

OTHER PUBLICATIONS

Cesario et al., "The absolute configuration of C–25 epimers of 25, 26–dihydroxycholecalciferol by X–ray differaction analysis", Tetrahedron Letters, No. 12, pp. 1097–1098, 1978.

Lam et al., "Synthesis and Biological Activity of 25E, 26–Dihydroxycholecalciferol", Steroids, vol. 25, No. 2, Feb. 1975, pp. 247–256.

Partridge et al., "Synthesis and Structure Proof of a Vitamin $D_3$ Metabolite, 25(S), 26–Dihydroxycholecalciferol", Journal of the American Chemical Society, vol. 103, No. 5, Mar. 11, 1981, pp. 1253–1255.

Koizumi et al., "Stereoselective Introduction of Hydroxy Groups into the Cholesterol Side Chain. Preparation of (24R)– and (24S)–24, 25–Dihydroxy– and (25R)– and (25S)–25, 26–Dihydroxyvitamin $D_3$ by Asymmetric Synthesis", Journal of the Chemical Society, Perkin Transactions 1., No. 7, 1983, pp. 1401–1410.

Barner et al., "Configuration of the Vitamin–$D_3$–Metabolite 25, 26–Dihydroxycholecalciferol: Synthesis of (25S,26)– and (25R,26)– Dihydroxycholecalciferol", Helvetica Chimica Acta, vol. 64, No. 3, 1981, pp. 915–938.

Ishiguro et al., "Stereoselective Introduction of Hydroxy––groups into the 24–, 25–, and 26– Positions of the Cholesterol Side Chain", Journal of the Chemical Society, Chemical Communications, No. 3, 1981, pp. 115–117.

Sasaki et al., "Manufacture of vitamin D with Actinomycetes", Chemical Abstracts, vol. 118, No. 17, Apr. 26, 1993, Abstract No. 167619 and JP 04 356 190 A.

Database WPI, Section Ch, Week 9304, Derwent Publications Ltd., London, GB; Class B01, AN 93–030367, XP002070167 and JP 04 356 190 A (Taisho Pharm. Co. Ltd.).

Database WPI, Section Ch, Week 9528, Derwent Publications Ltd., London, GB; Class B01, AN 95–211636, XP002070168 and JP 07 123 997 A (Chugai Pharm. Co. Ltd.).

*Primary Examiner*—Irene Marx
*Attorney, Agent, or Firm*—Wenderoth, Lind & Ponack, L.L.P.

[57] ABSTRACT

A method for preparing at least one hydroxycholesterol chosen from the group consisting of 25-hydroxycholesterol, 17,25-dihydroxycholesterol and 25,26-dihydroxycholesterol by biological hydroxylation of cholesterol, and the aforementioned dihydroxycholesterols. In the above biological hydroxylation, a microorganism is used which has the abovementioned hydroxylation capacity and which belongs to the genus Amycolata and the genus Sphingomonas.

4 Claims, No Drawings

PROCESS FOR PRODUCING HYDROXYLATED CHOLESTEROLS AND DIHYDROXYCHOLESTEROLS USING AMYCOLATA

This application was filed under 35 USC 371 as the national phase of PCT/JP96/02369 filed Aug. 26, 1996.

TECHNICAL FIELD

The present invention relates to a method for hydroxylating cholesterol by the action of microorganisms, and more specifically to a method for preparing one or more of either 25-hydroxycholesterol, 17,25-dihydroxycholesterol or 25,26-dihydroxycholesterol from cholesterol. The invention also relates to the aforementioned new dihydroxycholesterols.

BACKGROUND ART

For a biological method, in particular, a method for preparing hydroxy-derivatives of steroids including cholesterol by means of microorganisms, a method by which cholesterol is converted into 25-hydroxycholesterol using microorganisms of the genus Streptomyces has been disclosed in Japanese Laid-Open Patent Publication No. 123997/95. Also, in the biological conversion, which is interesting, of compounds other than steroids, there are known the methods for preparing 25-hydroxyvitamin D compounds by the hydroxylation of vitamin D compounds using microorganisms, for example, *Nocardia autotrophica, Streptomyces roseosporus, Amycolata saturnea, Amycolata autotrophica,* Sphingomonas sp. (Japanese Laid-Open Patent Publication Nos. 166090/92, 241197/95).

It is known that cholesterol may be, for example, an intermediate on the chemical synthesis of various kinds of vitamin D compounds (Yuki Gosei Kagaku (Organic Synthetwic Chemistry) 37, 809–829 (1979)), and compounds wherein one or more of the specific sites of cholesterol is/are hydroxylated beforehand may be expected for their use as intermediates on the synthesis of various hydroxylated vitamin D compounds. Indeed, according to the conversion method using microorganisms described in the abovementioned Japanese Laid-Open Patent Publication No. 123997/95, it has been published that cholesterol can be selectively hydroxylated at the 25-position which is preferable in relation to activated vitamin D.

However, the hydroxylation efficiency, according to the method described in said patent publication, is not always satisfactory. From the view point of improving the water-solubility of final compounds derived from cholesterol, for example, vitamin D compounds, it would be also desired to provide not only mono-hydroxylated cholesterols but also further hydroxylated cholesterols, for example, dihydroxylated cholesterols.

The purpose of the present invention is therefore to provide a method for efficiently preparing mono-hydroxylated cholesterols, in particular 25-hydroxycholesterol, and a method for preparing further hydroxylated dihydroxycholesterols, and new dihydroxycholesterols per se.

DISCLOSURE OF INVENTION

In the course of intensive study for the accomplishment of the above purpose, the present inventors have found that microorganisms of genera other than the genus Streptomyces described in the abovementioned Japanese Laid-Open Patent Publication No. 123997/95 hydroxylate cholesterol not only at the 25-position but also at the 17- or 26-position.

Thus, the above purpose can be achieved by providing a method, by which cholesterol having formula (I)

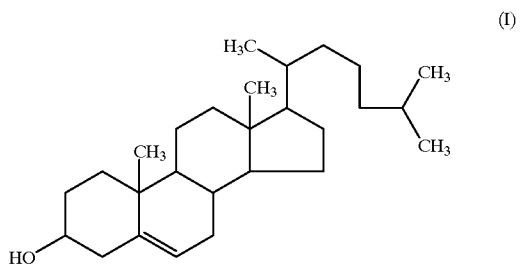

is biologically converted into hydroxylated cholesterols of formula (II)

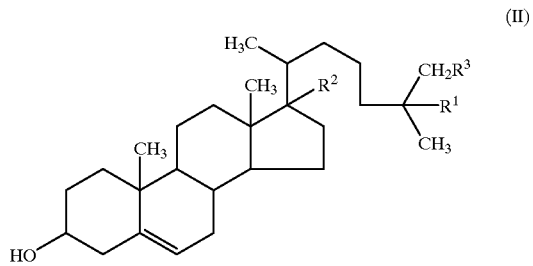

(in which $R^1$ is a hydroxyl radical, and $R^2$ and $R^3$ are a hydroxyl radical and a hydrogen atom, respectively, or a hydrogen atom and a hydroxyl radical, respectively), for preparing hydroxylated cholesterols having the formula (II), according to the invention, comprising (A) a step in which the aforementioned biological conversion can be carried out, and in which cholesterol having the formula (I) is treated by incubation in the presence of a microorganism, chosen from those that belong to the genus Amycolata and the genus Sphingomonas, or its preparation from cultures and oxygen, and (B) a step in which at least one of the hydroxylcholesterols having the formula (II) is recovered from the incubation-treated solution.

Among the hydroxylated cholesterols having the formula (II), dihydroxycholesterols of formula (II-b)

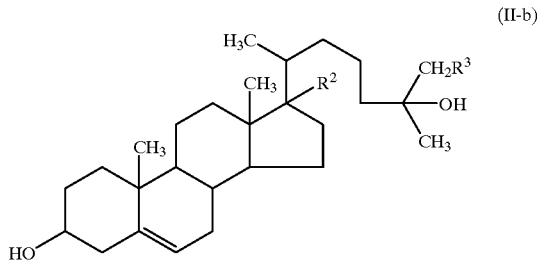

(in which $R^2$ and $R^3$ are a hydroxyl radical and a hydrogen atom, respectively, or a hydrogen atom and a hydroxyl radical, respectively) can be also prepared by another method in which 25-hydroxycholesterol is substituted for cholesterol as a starting material in the above method.

Furthermore, dihydroxycholesterols having the above formula (II-b), that is, 17,25-dihydroxycholesterol and 25,26-dihydroxycholesterol, are compounds that have not been published in literature in the prior art. Therefore, according to the present invention, new compounds, dihydroxycholesterols having the formula (II-b), are also provided.

DETAILED DESCRIPTION OF THE INVENTION

In the biological conversion according to the present invention, microorganisms and their preparations from cultures can be used, regardless of the kinds of species and strains, provided that they are microorganisms belonging to the genus Amycolata and the genus Sphingomonas and having the capacity to convert cholesterol of the above formula (I) into hydroxylated cholesterols of the formula (II). Mention can be made, as preferred microorganisms, *Amycolata saturnea* having the abovementioned conversion capacity, in particular, the microorganisms that have been deposited at the National Institute of Bioscience and Human Technology, the Agency of Industrial Science and Technology, the Ministry of International Trade and Industry in Japan with the deposition numbers of FERM BP-5544 and FERM BP-2307, and *Amycolata autotrophica*, in particular, the strain that has been deposited at American Type Culture Collection in the United States with the deposition number of ATCC 33796.

Species that belong to the genus Sphingomonas, *mali* IFO 15500, *paucimobilis* IFO 13935, *parapaucimobilis* IFO 15100, *yanoikuyae* IFO 15102, *adhaesiva* IFO 15099, *capsulata* IFO 12533, *sanguis* IFO 13937, *macrogoltabidus* IFO 15033 and *terrae* IFO 15098, although they are inferior in conversion capacity compared to that of microorganisms belonging to the above-described genus Amycolata, can be also used. Here, IFO is a deposition number in the Institute for Fermentation in Japan.

According to the invention, cholesterol (the compound of formula (I)) and/or 25-hydroxycholesterol (the compound of formula (II-a)) being a starting material (or a substrate) will be treated by incubation in the presence of any of said strains or their mycelia from cultures and oxygen. This treatment can be carried out by adding a substrate, at the time of the cultivation of the above strain under the aerobic conditions, into a culture solution, or optionally by adding a substrate into a suspension of, for example, the mycelia as such or the homogenized preparations obtained from cultures of the above strains, followed by incubation with oxygen, for example, with air. The addition of a substrate into a culture solution may be performed either before the cultivation or at a certain period of time after the cultivation. The above mycelia can be prepared by inoculating any of the above strains into a medium containing nutrient sources, followed by aerobic cultivation.

The cultivation of a strain to obtain such bacterial preparation from cultures or the cultivation of a strain carried out with the addition of a substrate can be performed, in principle, in accordance with cultivation methods for general microorganisms, but it is usually preferable to be carried out under aerobic conditions such as shaking liquid culture, aerated and stirred culture, etc.

The media used for the cultivation may be those containing nutrient sources which can be utilized by microorganisms belonging to the genus Amycolata and the genus Sphingomonas, and any of various kinds of synthetic or semi-synthetic media, natural media and the like can be used. For the medium compositions, glucose, maltose, xylose, fructose, sucrose and the like can be used alone or in combination as carbon sources. For nitrogen sources, organic nitrogen sources such as peptone, meat extract, soybean meal, casein, amino acids, yeast extract, urea and the like, and inorganic nitrogen sources such as sodium nitrate, ammonium sulfate and the like can be used alone or in combination. Furthermore, if necessary, for example, salts such as sodium chloride, potassium chloride, calcium carbonate, magnesium sulfate, sodium phosphate, potassium phosphate, cobalt chloride and the like, salts of heavy metals, vitamins can also be used. In case where foaming is furious during the cultivation, various known defoamers can be also added suitably into a medium.

Cultivation conditions can be suitably selected so that said strains can grow well. Usually, the cultivation are performed at pH 6–7.5, at 28–30° C. for approximately 2–8 days. Various cultivation conditions described above can be suitably changed depending on the kind and property of a microorganism used, external conditions and the like, and optimized conditions can be easily selected by those skilled in the art.

Alternatively, after completion of the cultivation, bacterial preparation from cultures is prepared by suspending mycelia, which has been separated by centrifugation or filtration, or homogenized mycelia in an appropriate solution. Solutions that can be used for suspending mycelia are the media as described above or buffer solutions such as tris-acetate, tris-hydrochloride, sodium succinate, sodium citrate, sodium phosphate, potassium phosphate and the like and they are used alone or in admixture. For the pH values of the buffer solution, preferably 6.0–9.0 and more preferably 7.0–8.5 can be mentioned.

A substrate can be added into a culture solution or a bacterial suspension in the form of powder or by dissolving in water-soluble organic solvent, for example, ethanol and the like, and the amount to be added, for example, in the case of a culture solution, is preferably 0.15–0.60 mg per 1 ml of the culture solution. When the amount is increased to more than 0.60 mg/ml, conversion rate becomes slow and is not preferable. After the addition of a substrate, the substrate can be converted into an objective hydroxylated cholesterol by carrying out the operation of shaking or aeration-agitation and the like at 27–31° C. for 1–3 days, preferably approximately for one day, to allow the reaction to proceed under aerobic conditions. In such a conversion reaction, the conversion rate into an objective hydroxylated cholesterol from a substrate can be remarkably increased by adding the substrate and methylated cyclodextrins to a reaction solution.

In a preferred embodiment according to the invention, the incubation treatment described above is therefore carried out further in the presence of methylated cyclodextrins.

Methylated cyclodextrins used according to the invention refer to compounds wherein hydrogen atoms of hydroxyl radicals at the 2-, 3- or 6-position of cyclodextrin are substituted by methyl radicals, and hexakis-(2,6-O-dimethyl)-α-cyclodextrin, derived from α-cyclodextrin, heptakis-(2,6-O-dimethyl)-β-cyclodextrin derived from β-cyclodextrin and octakis-(2,6-O-dimethyl)-γ-cyclodextrin derived from γ-cyclodextrin, which are completely methylated at the 2- and 6-positions, or hexakis-(2,3,6-O-trimethyl)-α-cyclodextrin derived from α-cyclodextrin, heptakis-(2,3,6-O-trimethyl)-β-cyclodextrin derived from β-cyclodextrin and octakis-(2,3,6-O-trimethyl)-γ-cyclodextrin derived from γ-cyclodextrin, which are completely methylated at the 2-, 3- and 6-positions, or partially methylated cyclodextrins wherein each of 6, 7 or 8 hydroxyl radicals at the position of the 2-, 3- and 6-positions are partially methylated can be mentioned. In the present invention, one or more of any methylated cyclodextrins is/are selected from those described above and used, but, in particular, partially methylated cyclodextrin derived from β-cyclodextrin is preferably used.

The amount of methylated cyclodextins added is 0.5 mg or more, preferably 0.5–15 mg, and more preferably 1–10 mg per 1 ml of a reaction solution. When the amount of the methylated cyclodextrins added is less than 0.5 mg per 1 ml of a reaction solution, there are sometimes cases where the increase in conversion rate into an objective hydroxylated cholesterol does not become significant compared to that without the addition, and for the amount in the region of 15 mg, foaming takes place in some cases, and it may become necessary to use a defoamer etc. together.

In the method according to the invention, nonionic surfactants may be added into a reaction mixture so as not to decrease the conversion rate described above. Mention can be made, as such a surfactant, of polyoxyethylene.sorbitan fatty acid ester (e.g., Tween$^R$ 80 (Sigma)), sorbitan fatty acid ester (e.g., Span$^R$ 85 (Sigma)), polyoxyethylene ether (e.g., Brij$^R$ 96 (Sigma)) and Triton$^R$ X-100 (Sigma), nonylphenol (e.g., Nonypol$^R$ 45 (Sanyo Chemical Industries Ltd.), block copolymer of ethylene oxide-propylene oxide (e.g., Pluronic$^R$ L-61 (Asahi Denka Kogyo K. K.), and Dislex$^R$ (Nippon Oil and Fats Co. Ltd.) as an anionic surfactant, Trax$^R$ (Nippon Oil and Fats Co. Ltd.) and the like.

To isolate an objective hydroxylated cholesterol thus produced from a reaction mixture, various known purification procedures can be selected and carried out in combination. For example, it can be separated and purified by means of adsorption to hydrophobic adsorption resins and elusion, extraction with solvent using ethyl acetate, n-butanol etc., a column chromatography with silica gel etc. or thin layer chromatography, preparative high performance liquid chromatography using a reversed phase column and the like and these can be used alone or suitably in combination, or optionally used repeatedly.

An *Amycolata saturnea* FERM BP-5544, which is one of the strains being able to be used particularly advantageously in the abovementioned biological conversion, was isolated from soil by the present inventors, and named A-1246 strain, and it is a new strain as described below showing bacteriological properties as follows:

(1) Morphology

Vegetative mycelium develops well on synthetic or natural agar media and branches irregularly. No septum is observed. Spore chains are formed abundantly on glycerin-asparagine agar media, starch-inorganic salts agar media and the like. By microscopic observation, sporulating mycelium branches monopodially with straight spore chains. Usually, the spore chains have three or more spores, and the long spore chains are developed at the late growth phase of the culture with smooth surfaces. The spore is cylindrical in shape and 0.5–0.8×2.5–4.3 μm in size. Sclerotia, sporangia and flagellated spore are not observed.

(2) Growth on Various Media (30° C.)

(2-1) Sucrose-nitrate Agar Medium

Growth on the medium is moderate and the color of the reverse side of colonies is pale brown. Aerial mycelium forms moderately and colors creamy. No soluble pigment is produced.

(2-2) Glucose-asparagin Agar Medium

Growth on the medium is slightly poor and the color of the reverse side of colonies is creamy. Aerial mycelium forms moderately and colors white. No soluble pigment is produced.

(2-3) Glycerin-asparagin Agar Medium

Growth on the medium is good and the color of the reverse side of colonies is pale yellow. Aerial mycelium forms well and colors white. No soluble pigment is produced.

(2-4) Starch-inorganic Salts Agar Medium

Growth on the medium is moderate and the color of the reverse side of colonies is creamy. Aerial mycelium forms well and colors white. No soluble pigment is produced.

(2-5) Tyrosine Agar Medium

Growth on the medium is moderate and the color of the reverse side of colonies is reddish brown. Aerial mycelium forms well and colors creamy. Soluble pigment with pale reddish brown color is produced.

(2-6) Nutrient Agar Medium

Growth on the medium is good and the color of the reverse side of colonies is pale yellow. Aerial mycelium forms well and colors white. No soluble pigment is produced.

(2-7) Yeast-malt Extract Agar Medium

Growth on the medium is good and the color of the reverse side of colonies is pale yellow. Aerial mycelium forms slightly poorly and colors white. No soluble pigment is produced.

(2-8) Oatmeal Agar Medium

Growth on the medium is moderate and the color of the reverse side of colonies is creamy. Aerial mycelium forms slightly poorly and colors white. No soluble pigment is produced.

(2-9) Peptone.Yeast.Iron Agar Medium

Growth on the medium is moderate and the color of the reverse side of colonies is pale brown. Aerial mycelium forms moderately and colors creamy. No soluble pigment is produced.

(3) Physiological Properties (3-1) Temperature Range for Growth

When nutrient agar medium is used, good growth is observed at the temperature in the range of 20–30° C. There is no growth at 10° C. or below, and at 40° C. or above (3-2) Distinction Between Aerobic and Anaerobic: Aerobic (3-3) Liquefaction of Gelatin: Positive (3-3) Hydrolysis of Starch: Negative (3-4) Coagulation and Peptonization of Skim Milk: Both Negative (3-5) Formation of Melanin-like Pigment: Negative
(3-6) Nitrate Reduction: Negative
(4) Utilization of Carbon Sources When a carbon source is added onto Pridham.Godlieb agar medium and the growth is observed, any carbon sources of the followings: D-glucose, sucrose, D-xylose, inositol, D-mannitol, D-fructose, can be utilized. L-arabinose, L-rhamnose and raffinose cannot be utilized.

(5) Cell Wall Components

As a result of the analysis of cell wall components with whole bacterial lysate, the cell wall of this strain belongs to the type III according to the classification by Lechevalier (International Journal of Systematic Bacteriology, vol. 20, p435–443 (1970)). Mycolic acid is not contained.

It is apparent form the above bacteriological properties that this strain belongs to Actinomycetes, and when these properties were compared with those of known microorganisms reported in the International Journal of Systematic Bacteriology, Vol.36, p29–37 (1986), this strain was almost identical to *Amycolata saturnea*. As a result of the above, this strain is concluded to belong to *Amycolata saturnea*, and named an *Amycolata saturnea* A-1246 strain. After deposited at the National Institute of Bioscience and Human Technology, the Agency of Industrial Science and Technology in Japan as FERM P-15098 on Aug. 7, 1995, this strain was transferred to the International Depositary Authority in the institute and given the deposition number FERM BP-5544 in compliance with the provisions of the Budapest Convention on International Acknowledgement of the Deposition of Microorganisms for the purpose of Patent Proceedings.

The present invention is illustrated in more detail by the following Examples, which are not intended to limit the invention.

Unless mentioned otherwise, the percentages in the examples below represents percent by weight.

EXAMPLES 1–9

Conversion into 25-hydroxycholesterol from Cholesterol

One hundred ml of a seed culture medium consisting of 1.5% of glucose, 1.5% of Bacto®-soyton (Difco), 0.5% of corn steep liquor, 0.4% of sodium chloride and 0.2% of calcium carbonate (pH 7.0) was placed in a 500 ml Erlenmeyer flask and autoclaved at 120° C. for 20 minutes. This medium was inoculated with 2 ml of a frozen inoculum of an *Amycolata saturnea* A-1246 strain (FERM BP-5544) and shaking culture was carried out at 220 rpm for 48 hours at 28° C., thus a seed culture solution being prepared.

Fifty ml of a conversion culture medium consisting of 2.0% of glucose, 0.2% of yeast extract, 0.5% of peptone, 1.0% of soybean meal, 0.5% of corn steep liquor, 0.04% of potassium secondary phosphate, 0.04% of sodium chloride and 0.2% of calcium carbonate (pH 7.4) was then placed in a 250 ml Erlenmeyer flask and autoclaved at 120° C. for 20 minutes. This medium was inoculated with 1 ml of the seed culture solution prepared above and shaking culture was carried out at 220 rpm at 28° C. Fifteen mg of the substrate cholesterol and each compound which is shown in Table 1 were added 48 hours later, and the cultivation continued for further 72 hours.

The substrate and the like were added in the following way: Fifteen mg of cholesterol in the form of powder was added in Example 1. For Example 2, 150 mg of cholesterol was suspended in 4 ml of ethanol, dispersed by sonication, and 0.4 ml of the suspension was added. In Example 3, 150 mg of cholesterol was suspended in a mixture of 1 ml of Tween 80 (surfactant: Sigma) and 3 ml of ethanol, dispersed by sonication, and 0.4 ml of the suspension was added. In Examples 4, 5 and 6, there were added 15 mg of cholesterol, 1 ml of Tween 80 and 5.6 ml of a 1.5% aqueous solution of each cyclodextrin which was sterilized beforehand (121° C., 20 minutes). In Examples 7, 8 and 9, there were added 15 mg of cholesterol, 1 ml of Tween 80 and a 1.5% aqueous solution of partially methylated β-cyclodextrin (methylation rate 74%: Mercian Corp.), which was sterilized beforehand (121° C., 20 minutes), at each determined concentration.

Two ml of the culture solution obtained was collected into a centrifugation tube with a stopper, to which 0.5 ml of ethyl acetate was added, and stirring for 30 minutes and further centrifugation at 3000 rpm for 15 minutes separated off the ethyl acetate layer. Five μl of this was spotted onto a TLC plate (Silica gel 60 $F_{254}$: Merck), developed with chloroform:methanol=10:1 and stained with sulfuric acid. The spot indicating the same Rf value (approximately 0.5) as a standard product (Sigma) was scanned by Chromatoscanner (CS-920: Shimadzu Corp.), 25-hydroxycholesterol being quantified. The conversion rates into 25-hydroxycholesterol from cholesterol were summarized in Table 1.

TABLE 1

| Example No. | Coexisting substance | Concentration of coexisting substance (%) | Conversion rate (%) |
|---|---|---|---|
| 1 | — | — | 0.8 |
| 2 | Ethanol | 0.80 | 0.7 |
| 3 | Tween 80 | 0.20 | 0.7 |
| 4 | α-CD | 0.15 | 0.7 |
| 5 | β-CD | 0.15 | 0.7 |
| 6 | γ-CD | 0.15 | 0.8 |
| 7 | β-PMCD | 0.05 | 5.8 |
| 8 | β-PMCD | 0.10 | 10.3 |
| 9 | β-PMCD | 0.15 | 12.1 |

α-CD: α-cyclodextrin
β-CD: β-cyclodextrin
γ-CD: γ-cyclodextrin
β-PMCD: partially methylated β-cyclodextrin

EXAMPLES 10–19

Conversion into 25-hydroxycholesterol from Cholesterol (Effect of Alteration in the Reaction Time)

Fifty ml of the conversion culture medium described in Examples 1–9 was placed in a 250 ml Erlenmeyer flask and autoclaved at 120° C. for 20 minutes. This medium was inoculated with 1 ml of the seed culture solution prepared as in Examples 1–9 and shaking culture was carried out at 220 rpm for 48 hours at 28° C. To this culture, 15 mg of cholesterol in the form of powder and 1 ml of Tween 80 were added, a 1.5% aqueous solution of each methylated β-cyclodextrin which was sterilized beforehand was further added so as to be a final concentration of 0.15%, and the cultivation continued. At 16, 40 and 64 hours after the addition of cholesterol, 25-hydroxycholesterol in the culture solution was quantified by the same method as Examples 1–9. The conversion rates into 25-hydroxycholesterol from cholesterol were summarized in Table 2. In Examples 17 and 18, the mixtures of 2,6-di-O-methyl-β-cyclodextrin and 2,4,6-tri-O-methyl-β-cyclodextrin were used at the ratios of 2:1 and 1:2, respectively.

TABLE 2

| Example No. | Coexisting substance | Methylation rate (%) | Conversion rate (%) 16 hr | 40 hr | 64 hr |
|---|---|---|---|---|---|
| 10 | — | — | 0.0 | 0.5 | 0.8 |
| 11 | β-PMCD | 56 | 11.6 | 7.6 | 10.5 |
| 12 | β-PMCD | 62 | 13.1 | 10.3 | 9.6 |
| 13 | β-PMCD | 68 | 11.3 | 10.4 | 10.7 |
| 14 | β-PMCD | 69 | 8.1 | 6.2 | 6.9 |
| 15 | β-PMCD | 74 | 13.5 | 7.6 | 10.5 |
| 16 | β-DMCD | 67 | 10.8 | 8.5 | 7.9 |
| 17 | β-DMCD + TMCD | 78 | 17.1 | 14.0 | 16.0 |
| 18 | β-DMCD + TMCD | 89 | 11.6 | 11.4 | — |
| 19 | β-TMCD | 100 | 0.0 | 2.9 | 4.3 |

β-PMCD: partially methylated β-cyclodextrin
β-DMCD: 2,6-di-O-methyl-β-cyclodextrin
β-TMCD: 2,4,6-tri-O-methyl-β-cyclodextrin

EXAMPLES 20–23

Conversion into 25-hydroxycholesterol from Cholesterol (Effect of Alteration in the Concentration of Cholesterol Added)

Fifty ml of the conversion culture medium described in Examples 1–9 was placed in a 250 ml Erlenmeyer flask and autoclaved at 120° C. for 20 minutes. This medium was inoculated with 1 ml of the seed culture solution prepared as in Examples 1–9 and shaking culture was carried out at 220 rpm for 48 hours at 28° C. To this culture were added cholesterol in the form of powder and 5.6 ml of a 1.5% aqueous solution of partially methylated β-cyclodextrin (methylation rate 74%: Mercian Corp.) which was sterilized beforehand, and the cultivation continued for further 40 hours. By the same method as Examples 1–9, 25-hydroxycholesterol in the culture solution obtained was quantified. The conversion rates into 25-hydroxycholesterol from cholesterol were summarized in Table 3.

TABLE 3

| Example No. | Concentration of CHO added | Concentration of 25OH—CHO produced | Conversion rate (%) |
|---|---|---|---|
| 20 | 0.15 mg/ml | 32 μg/ml | 21.3 |
| 21 | 0.30 mg/ml | 55 μg/ml | 18.3 |
| 22 | 0.60 mg/ml | 34 μg/ml | 5.6 |
| 23 | 1.20 mg/ml | 5 μg/ml | 0.4 |

CHO: Cholesterol
25OH—CHO: 25-hydroxycholesterol

EXAMPLES 24–26

Conversion into 25-hydroxycholesterol from Cholesterol (by Bacterial Preparations)

Fifty ml of the conversion culture medium described in Examples 1–9 was placed in a 250 ml Erlenmeyer flask and autoclaved at 120° C. for 20 minutes. This medium was inoculated with 1 ml of the seed culture solution prepared as in Examples 1–9 and shaking culture was carried out at 220 rpm for 48 hours at 28° C. The resulting culture solution was centrifuged (3000 rpm, 10 minutes) to collect the mycelia, which was then suspended in 50 ml of each buffer solution having the following compositions.

Buffer Solution A (Example 24)
50 mM tris-acetate, 25 mM sodium succinate, 0.05% magnesium sulfate, 0.15% partially methylated β-cyclodextrin (methylation rate 74%: Mercian Corp.), 0.5% glucose (pH 8.0)

Buffer Solution B (Example 25)
50 mM tris-acetate, 25 mM sodium succinate, 0.05% magnesium sulfate, 0.15% partially methylated β-cyclodextrin (methylation rate 74%: Mercian Corp.) (pH 8.0)

Buffer Solution C (Example 26)
50 mM tris-acetate, 25 mM sodium succinate, 0.05% magnesium sulfate (pH 8.0)

Fifteen mg of cholesterol in the form of powder was added into each of these suspensions, and the mixture was incubated with shaking at 220 rpm for 24 hours at 28° C. By the same method as Examples 1–9, 25-hydroxycholesterol in the resulting solution was quantified. The conversion rates into 25-hydroxycholesterol from cholesterol were summarized in Table 4.

TABLE 4

| Example No. | Buffer solution | Conversion rate (%) |
|---|---|---|
| 24 | Buffer solution A | 13.8 |
| 25 | Buffer solution B | 15.4 |
| 26 | Buffer solution C | 0.5 |

EXAMPLE 27

Conversion into 25-hydroxycholesterol from Cholesterol (Scale Up)

One hundred ml of a seed culture medium consisting of 1.5% of glucose, 1.5% of Bacto®-soyton (Difco), 0.5% of corn steep liquor, 0.4% of sodium chloride and 0.2% of calcium carbonate (pH 7.0) was placed in a 500 ml Erlenmeyer flask and autoclaved at 120° C. for 20 minutes. This medium was inoculated with 2 ml of a frozen inoculum of an *Amycolata saturnea* A-1246 strain (FERM BP-5544) and shaking culture was carried out at 220 rpm for 48 hours at 28° C., thus a seed culture solution being prepared.

Then, 1.5 l of a conversion culture medium consisting of 2.0% of glucose, 0.2% of yeast extract, 0.5% of peptone, 1.0% of soybean meal, 0.5% of corn steep liquor, 0.04% of potassium secondary phosphate, 0.04% of sodium chloride, 0.2% of calcium carbonate and 0.05% of Silicon KM75 (defoamer: Shin-Etsu Chemical Co., Ltd.) (pH 7.4) was placed in each of five 3 l mini-jar and sterilized by heating at 120° C. for 20 minutes. Each medium was inoculated with 30 ml of the seed culture solution prepared above and cultivation was carried out for 48 hours at the temperature of 28° C., at the agitation of 400 rpm and at the aeration of 1.0 vvm. To this culture, 450 mg of cholesterol dissolved in 15 ml of ethanol was added, 4 ml of a 10% aqueous solution of Silicon KM75 (defoamer) and 30 ml of a 7.5% aqueous solution of partially methylated β-cyclodextrin (methylation rate 74%: Mercian Corp.) were further added, and the cultivation continued for further 72 hours. The concentration of 25-hydroxycholesterol quantified by the same method as Example 1 was 114 μg/ml at 24 hours, 62 μg/ml at 48 hours, and 49 μg/ml at 72 hours after the addition of cholesterol. Thus, 5.6 l of combined culture solution was obtained from five mini-jars.

Following the addition of Pearlite (filter aid: Toko Pearlite IND.) at a concentration of 3%, this culture solution was filtrated to obtain filtrate. Five l of ethyl acetate and 500 g of sodium chloride were added and the mixture was stirred for 90 minutes by a stirrer. Two hundreds ml of ethanol was further added and the mixture allowed to stand for 1 hour. After the ethyl acetate layer (about 4.5 l) was separated off and concentrated under reduced pressure to a volume of approximately 50 ml, 50 ml of ethyl acetate, 5 g of sodium chloride and 2 ml of ethanol were further added to extract the product into the organic layer. After the ethyl acetate layer (about 50 ml) was separated off and concentrated under reduced pressure to a volume of approximately 4 ml, 50 ml of deionized water was added. The resulting suspension was extracted twice with 30 ml of chloroform. The chloroform layer was dried over anhydrous sodium sulfate and concentrated to dryness, giving 800 mg of yellow powder.

The resulting powder was dissolved in the lower layer of chloroform-methanol-water (7:13:8) and purified by centrifuged liquid-liquid partition chromatography (CPC model NMF, 250W×12: Sanki Engineering Co., Ltd.) using this two-layer system: Portions where a spot was observed at the Rf value of about 0.5 in the TLC analysis as in Example 1 were collected and concentrated to dryness, giving 168.2 mg of white powder. This powder was further subjected to column chromatography on Sephadex$^R$ LH-20 (Pharmacia, developing solvent: toluene-methanol (85:15)) and fractions that gave single spot in the above TLC analysis were combined and concentrated to dryness, giving 133.5 mg of 25-hydroxycholesterol in the form of white powder.

The resulting powder was dissolved in methanol at a concentration of 0.1 mg/ml and subjected to a HPLC analysis under the following conditions, single peak with the retention time of about 17.9 minutes being observed. This retention time was in agreement with that of a standard product of 25-hydroxycholesterol (Sigma).

(HPLC Conditions)

Column: YMC pack A-302 (φ 4.6 mm×150 mm)

Mobile phase: 85% methanol

Flow rate: 0.8 ml/minute

Detection: 210 nm

Mass spectrum and NMR spectrum of the resulting powder were also in agreement with those of the standard product.

(1) FAB mass spectrum (positive ion, matrix NBA): m/z=402 (M$^+$)

(2) $^1$H-NMR spectrum (CDCl$_3$: internal standard TMS): 0.68 (3H, s), 0.93 (3H, d, J=6.2 Hz), 1.01 (3H, s), 1.22 (6H, s), 3.53 (1H, m), 5.35 (1H, m)

EXAMPLE 28

Conversion into 17,25-dihydroxycholesterol from Cholesterol

A seed culture solution was prepared as in Examples 1–9.

Then, 1.5 l of a conversion culture medium consisting of 2.0% of glucose, 0.2% of yeast extract, 0.5% of peptone, 1.0% of soybean meal, 0.5% of corn steep liquor, 0.04% of potassium secondary phosphate, 0.04% of sodium chloride, 0.2% of calcium carbonate and 0.05% of Silicon KM75 (defoamer: Shin-Etsu Chemical Co., Ltd.) (pH 7.4) was placed in a 3 l mini-jar and sterilized by heating at 120° C. for 20 minutes. This medium was inoculated with 30 ml of the seed culture solution prepared above and cultivation was carried out for 48 hours at the temperature of 28° C., at the agitation of 400 rpm and at the aeration of 1.0 vvm. To this culture, 450 mg of cholesterol dissolved in 15 ml of ethanol was added, 4 ml of a 10% aqueous solution of Silicon KM75 (defoamer: Shin-Etsu Chemical Co., Ltd.) and 30 ml of a 7.5% aqueous solution of partially methylated β-cyclodextrin (methylation rate 74%: Merican Corp.) were further added, and the cultivation continued for further 91 hours.

Following the addition of Pearlite (filter aid: Toko Pearlite IND.) at a concentration of 3%, the culture solution thus obtained was filtrated to give 1.2 l of filtrate. The filtrate was passed through a 100 ml Amberlite XAD-8 (Rohm & Haas) column to adsorb the product. After washing this column with 200 ml of 20% methanol, the product was eluted with 500 ml of 90% aqueous methanol. After concentrating the eluate under reduced pressure to remove methanol, about 100 ml of the residual water layer was extracted twice with 50 ml of ethyl acetate. The resulting ethyl acetate layer was dried over anhydrous sodium sulfate and concentrated to dryness.

After applying this residue to a 100 ml silica gel (trade name: Silica gel 60, Merck) column, eluting with 400 ml of chloroform-methanol (100:1) and concentrating the eluate to dryness to remove the solvent, the residue was further subjected to preparative thin layer chromatography (trade name: Silica gel 60 Art11798, Merck) and developed with chloroform-methanol (20:1). The portion corresponding to 17,25-dihydroxycholesterol (Rf=0.33) was scraped off, extracted with chloroform-methanol (1:1) and concentrated to dryness, giving 3.3 mg of 17,25-dihydroxycholesterol in the form of white powder.

The physical and chemical properties of 17,25-dihydroxycholesterol provided according to the present invention were shown below:

(1) Appearance: white powder (2) Molecular formula: $C_{27}H_{46}O_3$ (3) FAB mass spectrum (negative ion, matrix NBA): m/z=417 (M-1)

(4) $^1$H-NMR spectrum (400 MHZ, CDCl$_3$): Main absorptions were as follows:

δ TMS (ppm): 0.78 (3H, s), 0.92 (3H, d, J=6.2 Hz), 1.00 (3H, s), 1.22 (6H, s), 3.53 (1H, m), 5.36 (1H, m)

(5) $^{13}$C-NMR spectrum (100 MHz, CDCl$_3$): Main absorptions were as follows:

δ TMS (ppm): 14.0 (q), 14.4 (q), 19.4 (q), 20.9 (t), 22.6 (t), 23.7 (t), 29.3 (q×2), 31.7 (t), 31.9(t), 32.2 (d), 32.3 (t), 32.7 (t), 36.5 (s), 37.3 (t), 38.1 (t), 39.7 (d), 42.3 (t), 44.2 (t), 47.3 (s), 49.7 (d), 51.2 (d), 71.0 (s), 71.8 (d), 86.5 (s), 121.7 (d), 140.7 (s)

EXAMPLES 29–37

Preparation of 17,25-dihydroxycholesterol (Effect of Alteration in the Coexisting Substance on Conversion Rate)

One hundred ml of a seed culture medium consisting of 1.5% of glucose, 1.5% of Bacto®-soyton (Difco), 0.5% of corn steep liquor, 0.4% of sodium chloride and 0.2% of calcium carbonate (pH 7.0) was placed in a 500 ml Erlenmeyer flask and autoclaved at 120° C. for 20 minutes. This medium was inoculated with 2 ml of a frozen inoculum of an *Amycolata saturnea* A-1246 strain (FERM BP-5544) and shaking culture was carried out at 220 rpm for 48 hours at 28° C., thus seed culture solution being prepared.

Fifty ml of a conversion culture medium consisting of 2.0% of glucose, 0.2% of yeast extract, 0.5% of peptone, 1.0% of soybean meal, 0.5% of corn steep liquor, 0.04% of potassium secondary phosphate, 0.04% of sodium chloride and 0.2% of calcium carbonate (pH 7.4) was then placed in a 250 ml Erlenmeyer flask and autoclaved at 120° C. for 20 minutes. This medium was inoculated with 1 ml of the seed culture solution prepared above and shaking culture was carried out at 220 rpm at 28° C. Fifteen mg of the substrate cholesterol and each compound which is shown in Table 5 were added 48 hours later, and the cultivation continued for further 72 hours.

The substrate and the like were added in the following way: Fifteen mg of cholesterol in the form of powder was added in Example 29. For Example 30, 150 mg of cholesterol was suspended in 4 ml of ethanol, dispersed by sonication, and 0.4 ml of the suspension was added. In Example 31, 150 mg of cholesterol was suspended in a mixture of 1 ml of Tween 80 (surfactant: Sigma) and 3 ml of ethanol, dispersed by sonication, and 0.4 ml of the suspension was added. In Examples 32, 33 and 34, there were added 15 mg of cholesterol, 1 ml of Tween 80 and 5.6 ml of a 1.5% aqueous solution of each cyclodextrin which was sterilized beforehand (121° C., 20 minutes). In Examples 35, 36 and 37, there were added 15 mg of cholesterol, 1 ml of Tween 80 and a 1.5% aqueous solution of partially methylated β-cyclodextrin (methylation rate 74%: Mercian Corp.), which was sterilized beforehand (121° C., 20 minutes), at each determined concentration.

Two ml of the culture solution obtained was collected into a centrifugation tube with a stopper, to which 0.5 ml of ethyl acetate was added, and stirring for 30 minutes and further centrifugation at 3000 rpm for 15 minutes separated off the ethyl acetate layer. Five μl of this was spotted onto a TLC plate (Silica gel 60 $F_{254}$: Merck), developed with chloroform:methanol=10:1 and stained with sulfuric acid. The spot indicating the same Rf value (0.33) as the standard product in Example 1 was scanned by Chromatoscanner (CS-920: Shimadzu Corp.), 17,25-hydroxycholesterol being quantified. The conversion rates into 17,25-dihydroxycholesterol from cholesterol were summarized in Table 5.

TABLE 5

| Example No. | Coexisting substance | Concentration of coexisting substance (%) | Conversion rate (%) |
|---|---|---|---|
| 29 | — | — | 0.3 |
| 30 | Ethanol | 0.80 | 0.2 |
| 31 | Tween 80 | 0.20 | 0.2 |
| 32 | α-CD | 0.15 | 0.3 |
| 33 | β-CD | 0.15 | 0.2 |
| 34 | γ-CD | 0.15 | 0.3 |
| 35 | β-PMCD | 0.05 | 2.0 |
| 36 | β-PMCD | 0.10 | 2.8 |
| 37 | β-PMCD | 0.15 | 3.5 |

α-CD: α-cyclodextrin
β-CD: β-cyclodextrin
γ-CD: γ-cyclodextrin
β-PMCD: partially methylated β-cyclodextrin

EXAMPLES 38–47

Preparation of 17,25-dihydroxycholesterol (Effect of Alteration in the Reaction Time)

Fifty ml of the conversion culture medium described in Examples 29–37 was placed in a 250 ml Erlenmeyer flask and autoclaved at 120° C. for 20 minutes. this medium was inoculated with 1 ml of the seed culture solution prepared as in Example 2 and shaking culture was carried out at 220 rpm for 48 hours at 28° C. Fifteen mg of cholesterol in the form of powder and 1 ml of Tween 80 were added to this culture, a 1.5% aqueous solution of each methylated β-cyclodextrin which was sterilized beforehand was further added so as to be a final concentration of 0.15%, and the cultivation continued. At 16, 40 and 64 hours after the addition of cholesterol, 17,25-hydroxycholesterol in the culture solution was quantified by the same method as Examples 29–37. The conversion rates into 17,25-dihydroxycholesterol from cholesterol were summarized in Table 6. In Examples 45 and 46, the mixtures of 2,6-di-O-methyl-β-cyclodextrin and 2,4,6-tri-O-methyl-β-cyclodextrin were used at the ratios of 2:1 and 1:2, respectively.

TABLE 6

| Example No. | Coexisting substance | Methylation rate (%) | Conversion rate (%) | | |
|---|---|---|---|---|---|
| | | | 16 hr | 40 hr | 64 hr |
| 38 | — | — | 0.0 | 0.1 | 0.3 |
| 39 | β-PMCD | 56 | 2.6 | 3.7 | 0.0 |
| 40 | β-PMCD | 62 | 2.9 | 4.2 | 2.5 |
| 41 | β-PMCD | 68 | 2.8 | 3.3 | 2.5 |
| 42 | β-PMCD | 69 | 2.9 | 0.0 | 2.2 |
| 43 | β-PMCD | 74 | 2.9 | 1.8 | 2.6 |
| 44 | β-DMCD | 67 | 3.2 | 3.1 | 2.1 |
| 45 | β-DMCD + TMCD | 78 | 2.6 | 2.2 | 4.7 |
| 46 | β-DMCD + TMCD | 89 | 0.0 | 2.3 | — |
| 47 | β-TMCD | 100 | 0.0 | 0.1 | 0.2 |

β-PMCD: partially methylated β-cyclodextrin
β-DMCD: 2,6-di-O-methyl-β-cyclodextrin
β-TMCD: 2,4,6-tri-O-methyl-β-cyclodextrin

EXAMPLES 48–51

Preparation of 17,25-dihydroxycholesterol (Alteration in the Substrate Concentration)

Fifty ml of the conversion culture medium described in Examples 29–37 was placed in a 250 ml Erlenmeyer flask and autoclaved at 120° C. for 20 minutes. This medium was inoculated with 1 ml of the seed culture solution prepared as in Examples 29–37 and shaking culture was carried out at 220 rpm for 48 hours at 28° C. To this culture were added cholesterol in the form of powder and 5.6 ml of a 1.5% aqueous solution of partially methylated β-cyclodextrin (methylation rate 74%: Merican Corp.) which was sterilized beforehand, and the cultivation continued for further 40 hours. By the same method as Examples 29–37, 25-hydroxycholesterol in the resulting culture solution was quantified. The conversion rates into 17,25-dihydroxycholesterol from cholesterol were summarized in Table 7.

TABLE 7

| Example No. | Concentration of CHO added | Concentration of DiOH—CHO produced | Conversion rate (%) |
|---|---|---|---|
| 48 | 0.15 mg/ml | 28 μg/ml | 18.7 |
| 49 | 0.30 mg/ml | 16 μg/ml | 5.3 |
| 50 | 0.60 mg/ml | 6 μg/ml | 1.0 |
| 51 | 1.20 mg/ml | 0 μg/ml | 0.0 |

CHO: Cholesterol
DiOH—CHO: 17,25-dihydroxycholesterol

EXAMPLES 52

Preparation of 17,25-dihydroxycholesterol

A seed culture solution was prepared as in Examples 1–9.

Then, 1.5 l of a conversion culture medium consisting of 2.0% of glucose, 0.2% of yeast extract, 0.5% of peptone, 1.0% of soybean meal, 0.5% of corn steep liquor, 0.04% of potassium secondary phosphate, 0.04% of sodium chloride, 0.2% of calcium carbonate and 0.05% of Silicon KM75 (defoamer: Shin-Etsu Chemical Co., Ltd.) (pH 7.4) was placed in a 3 l mini-jar and sterilized by heating at 120° C. for 20 minutes. This medium was inoculated with 30 ml of the seed culture solution prepared above and cultivation was carried out for 48 hours at the temperature of 28° C., at the agitation of 400 rpm and at the aeration of 1.0 vvm. To this culture, 450 mg of cholesterol dissolved in 15 ml of ethanol was added, 4 ml of a 10% aqueous solution of Silicon KM75 (defoamer: Shin-Etsu Chemical Co., Ltd.) and 30 ml of a 7.5% aqueous solution of partially methylated β-cyclodextrin (methylation rate 74%: Merican Corp.) were further added, and the cultivation continued for further 91 hours.

Following the addition of Pearlite (filter aid: Toko Pearlite IND.) at a concentration of 3%, the culture solution thus obtained was filtrated to give 1.2 l of filtrate. This filtrate was passed through a 100 ml Amberlite XAD-8 (Rohm & Haas) column to adsorb the product. After washing this column with 200 ml of 20% aqueous methanol, the product was eluted with 500 ml of 90% aqueous methanol. After concentrating the eluate under reduced pressure to remove methanol, about 100 ml of the residual aqueous layer was extracted twice with 50 ml of ethyl acetate. The resulting ethyl acetate layer was dried over anhydrous sodium sulfate and concentrated to dryness.

After applying this residue to a 100 ml Silica gel (trade name: Silica gel 60, Merck) column, eluting with 400 ml of chloroform-methanol (100:1) and concentrating the eluate under reduced pressure to remove the solvent, the residue was further subjected to preparative thin layer chromatography (trade name: Silica gel 60 Art11798, Merck) and developed with chloroform-methanol (20:1). The portion corresponding to 25,26-dihydroxycholesterol (Rf=0.26) was scraped off, extracted with chloroform-methanol (1:1) and concentrated to dryness, giving 10.2 mg of 25,26-dihydroxycholesterol in the form of white powder.

The physical and chemical properties of 25,26-dihydroxycholesterol provided by the present invention were shown below:

(1) Appearance: white powder (2) Melting point: 185–191° C.

(3) Molecular formula: $C_{27}H_{46}O_3$ (4) FAB mass spectrum (negative ion, matrix NBA): m/z=417 (M-1)

(5) $^1$H-NMR spectrum (400 MHz, $CDCl_3$): Main absorptions were as follows:

δTMS (ppm): 0.69 (3H, s), 0.93 (3H, d, J=6.6 Hz), 1.01 (3H, s), 1.14 (3H, s), 3.37 (1H, d, J=11.0 Hz), 3.43 (1H, d, J=11.0 Hz), 3.50 (1H, m), 5.34 (1H, m)

(6) $^{13}$C-NMR spectrum (100 MHz, $CDCl_3$): Absorptions were as follows:

δTMS (ppm): 11.9 (q), 18.7 (q), 19.4 (q), 20.2 (t), 21.1 (t), 23.3 (q), 24.3 (t), 28.2 (t), 31.7 (t), 31.9 (t+d), 35.7 (d), 36.5 (s+t), 37.3 (t), 39.2 (t), 39.8 (t), 42.3 (t), 42.3 (t), 50.1 (d), 56.1 (d), 56.8 (d) 70.0 (t), 71.8 (d), 73.0 (s), 121.7 (d), 140.8 (s)

EXAMPLES 53–61

Preparation of 25,26-dihydroxycholesterol (Effect of the Additives)

A seed culture solution was prepared as in Examples 1–9.

Fifty ml of a conversion culture medium consisting of 2.0% of glucose, 0.2% of yeast extract, 0.5% of peptone, 1.0% of soybean meal, 0.5% of corn steep liquor, 0.04% of potassium secondary phosphate, 0.04% of sodium chloride and 0.2% of calcium carbonate (pH 7.4) was then placed in a 250 ml Erlenmeyer flask and autoclaved at 120° C. for 20 minutes. This medium was inoculated with 1 ml of the seed culture solution prepared above and shaking culture was carried out at 220 rpm at 28° C. Fifteen mg of the substrate cholesterol and each compound which is shown in Table 8 were added 48 hours later, and the cultivation continued for further 72 hours.

The substrate and the like were added in the following way: Fifteen mg of cholesterol in the powder form was added in Example 53. For Example 54, 150 mg of cholesterol was suspended in 4 ml of ethanol, dispersed by sonication, and 0.4 ml of the suspension was added. In Example 55, 150 mg of cholesterol was suspended in a mixture of 1 ml of Tween 80 (surfactant: Sigma) and 3 ml of methanol, dispersed by sonication, and 0.4 ml of the suspension was added. In Examples 56, 57 and 58, there were added 15 mg of cholesterol, 1 ml of Tween 80 and 5.6 ml of a 1.5% aqueous solution of each cyclodextrin which was sterilized beforehand (121° C., 20 minutes). In Examples 59, 60 and 61, there were added 15 mg of cholesterol, 1 ml of Tween 80 and a 1.5% aqueous solution of partially methylated β-cyclodextrin (methylation rate 74%: Mercian Corp.), which was sterilized beforehand (121° C., 20 minutes), at each determined concentration.

Two ml of the resulting culture solution was collected into a centrifugation tube with a stopper, to which 0.5 ml of ethyl acetate was added, and stirring for 30 minutes and further centrifugation at 3000 rpm for 15 minutes separated off the ethyl acetate layer. Five µl of this was spotted onto a TLC plate (Silica gel 60 $F_{254}$: Merck), developed with chloroform:methanol=10:1 and stained with sulfuric acid. The spot indicating the same Rf value (0.26) as the standard product in Example 1 was scanned by Chromatoscanner (CS-920: Shimadzu Corp.), 25,26-dihydroxycholesterol being quantified. The conversion rates into 25,26-dihydroxycholesterol from cholesterol were summarized in Table 8.

TABLE 8

| Example No. | Coexisting substance | Concentration of coexisting substance (%) | Conversion rate (%) |
|---|---|---|---|
| 53 | — | — | 0.1 |
| 54 | Ethanol | 0.80 | 0.2 |
| 55 | Tween 80 | 0.20 | 0.1 |
| 56 | α-CD | 0.15 | 0.3 |
| 57 | β-CD | 0.15 | 0.2 |
| 58 | γ-CD | 0.15 | 0.2 |
| 59 | β-PMCD | 0.05 | 1.8 |
| 60 | β-PMCD | 0.10 | 2.4 |
| 61 | β-PMCD | 0.15 | 3.0 |

α-CD: α-cyclodextrin
β-CD: β-cyclodextrin
γ-CD: γ-cyclodextrin
β-PMCD: partially methylated β-cyclodextrin

EXAMPLES 62–71

Preparation of 25,26-dihydroxycholesterol (Effect of the Reaction Time)

Fifty ml of the conversion medium described in Examples 53–61 was placed in a 250 ml Erlenmeyer flask and autoclaved at 120° C. for 20 minutes. This medium was inoculated with 1 ml of the seed culture solution prepared as in Examples 53–61 and shaking culture was carried out at 220 rpm for 48 hours at 28° C. To this culture, 15 mg of cholesterol in the form of powder and 1 ml of Tween 80 were added, a 1.5% aqueous solution of each partially methylated β-cyclodextrin which was sterilized beforehand was further added so as to be a final concentration of 0.15%, and the cultivation continued. At 16, 40 and 64 hours after the addition of cholesterol, 25,26-dihydroxycholesterol in the culture solution was quantified by the same method as Examples 53–61. The conversion rates into 25,26-dihydroxycholesterol from cholesterol were summarized in Table 9. In Examples 69 and 70, the mixture of 2,6-di-O-methyl-β-cyclodextrin and 2,4,6-tri-O-methyl-β-cyclodextrin were used at the ratios of 2:1 and 1:2, respectively.

TABLE 9

| Example No. | Coexisting substance | Methylation rate (%) | Conversion rate (%) 16 hr | 40 hr | 64 hr |
|---|---|---|---|---|---|
| 62 | — | — | 0.0 | 0.1 | 0.2 |
| 63 | β-PMCD | 56 | 3.3 | 2.5 | 0.0 |
| 64 | β-PMCD | 62 | 2.8 | 2.3 | 2.3 |
| 65 | β-PMCD | 68 | 3.3 | 3.0 | 3.2 |
| 66 | β-PMCD | 69 | 3.9 | 1.0 | 1.7 |
| 67 | β-PMCD | 74 | 2.2 | 2.5 | 2.6 |
| 68 | β-DMCD | 67 | 3.5 | 4.1 | 3.7 |
| 69 | β-DMCD + TMCD | 78 | 2.5 | 3.1 | 3.4 |
| 70 | β-DMCD + TMCD | 89 | 0.0 | 1.6 | — |
| 71 | β-TMCD | 100 | 0.0 | 0.1 | 0.2 |

β-PMCD: partially methylated β-cyclodextrin
β-DMCD: 2,6-di-O-methyl-β-cyclodextrin
β-TMCD: 2,4,6-tri-O-methyl-β-cyclodextrin

EXAMPLES 72–75

Preparation of 25,26-dihydroxycholesterol (Effect of the Substrate Concentration)

Fifty ml of the conversion culture medium described in Examples 53–61 was placed in a 250 ml Erlenmeyer flask and autoclaved at 120° C. for 20 minutes. This medium was inoculated with 1 ml of the seed culture solution prepared as in Examples 53–61 and shaking culture was carried out at 220 rpm for 48 hours at 28° C. To this culture were added cholesterol in the form of powder and 5.6 ml of a 1.5% aqueous solution of partially methylated β-cyclodextrin (methylation rate 74%: Mercian Corp.) which was sterilized beforehand, and the cultivation continued for further 40 hours. By the same method as Examples 53–61, 25,26-dihydroxycholesterol in the culture solution obtained was quantified. The conversion rates into 25,26-dihydroxycholesterol from cholesterol were summarized in Table 10.

TABLE 10

| Example No. | Concentration of CHO added | Concentration of DiOH—CHO produced | Conversion rate (%) |
|---|---|---|---|
| 72 | 0.15 mg/ml | 30 µg/ml | 20.0 |
| 73 | 0.30 mg/ml | 18 µg/ml | 6.0 |
| 74 | 0.60 mg/ml | 7 µg/ml | 1.2 |
| 75 | 1.20 mg/ml | 0 µg/ml | 0.0 |

CHO: Cholesterol
DiOH—CHO: 25,26-dihydroxycholesterol

EXAMPLES 76–88

A seed culture solution and a conversion culture medium were prepared similarly to those in Examples 1–9, except that a strain used was replaced with each strain which is shown in Table 11, and partially methylated β-cyclodextrin was added so as to be a final concentration of 1.0%.

The concentration of cholesterol added was made to be 300 µg/ml and the culture was carried out at the pH and the reaction time which are shown in Table 11 below. The measurements of the substrate cholesterol and the hydroxylated cholesterols obtained were carried out in accordance with those in the above Examples. The results were summarized in Table 11.

TABLE 11

| Example No. | Microorganism | Reaction time (hr) | pH | Residual CHO | 25(OH)—CHO | 17, 25(OH)—CHO | 25, 26(OH)—CHO | Conversion rate (%) |
|---|---|---|---|---|---|---|---|---|
| 76 (Comparison) | Streptomyces roseosporus | 18 | 8.21 | 168.00 | 15.90 | 0.00 | 0.00 | 5.3 |
| | | 46 | 8.57 | 0.00 | 0.00 | 0.00 | 0.00 | 0.0 |
| | | 68 | 8.83 | 0.00 | 22.60 | 0.00 | 0.00 | 7.5 |
| 77 | FERM BP-5544 | 18 | 7.56 | 14.20 | 250.00 | 0.00 | 0.00 | 83.3 |
| | | 48 | 7.58 | 0.00 | 290.00 | 23.10 | 28.70 | 96.7 |
| | | 68 | 7.97 | 0.00 | 269.00 | 22.10 | 39.30 | 89.7 |
| 78 | FERM BP-2307 | 18 | 7.56 | 15.80 | 261.00 | 0.00 | 0.00 | 87.0 |
| | | 46 | 7.56 | 0.00 | 289.00 | 21.80 | 25.00 | 96.3 |
| | | 68 | 7.90 | 0.00 | 240.00 | 19.00 | 23.10 | 80.0 |
| 79 | Amycolate autotrophica ATCC 33796 | 18 | 7.40 | 111.00 | 200.00 | 0.00 | 0.00 | 66.7 |
| | | 46 | 7.38 | 15.20 | 274.00 | 0.00 | 19.70 | 91.3 |
| | | 68 | 7.97 | 0.00 | 246.00 | 0.00 | 14.00 | 82.0 |
| 80 | Sphingomonas IFO 15500 | 18 | 7.06 | 265.00 | 0.00 | 0.00 | 0.00 | 0.0 |
| | | 46 | 7.07 | 316.00 | 26.90 | 3.83 | 0.00 | 9.0 |
| | | 68 | 7.05 | 259.00 | 0.00 | 0.00 | 0.00 | 0.0 |
| 81 | Sphingomonas IFO 13935 | 18 | 4.49 | 246.00 | 0.00 | 0.00 | 0.00 | 0.0 |
| | | 46 | 4.51 | 302.00 | 22.30 | 0.00 | 0.00 | 7.4 |
| | | 68 | 4.47 | 239.00 | 19.40 | 0.00 | 0.00 | 6.5 |
| 82 | Sphingomonas IFO 15100 | 18 | 4.92 | 228.00 | 0.00 | 0.00 | 0.00 | 0.0 |
| | | 46 | 4.76 | 302.00 | 13.40 | 0.00 | 0.00 | 4.5 |
| | | 68 | 4.68 | 244.00 | 28.30 | 0.00 | 0.00 | 9.4 |
| 83 | Sphingomonas IFO 15102 | 18 | 4.92 | 225.00 | 0.00 | 0.00 | 0.00 | 0.0 |
| | | 46 | 4.90 | 296.00 | 16.10 | 0.00 | 0.00 | 5.4 |
| | | 68 | 4.87 | 219.00 | 0.00 | 0.00 | 0.00 | 0.0 |
| 84 | Sphingomonas IFO 15099 | 18 | 7.11 | 210.00 | 0.00 | 0.00 | 0.00 | 0.0 |
| | | 46 | 5.38 | 274.00 | 0.00 | 0.00 | 0.00 | 0.0 |
| | | 68 | 5.05 | 167.00 | 10.90 | 0.00 | 0.00 | 3.6 |
| 85 | Sphingomonas IFO 12533 | 18 | 7.13 | 245.00 | 0.00 | 0.00 | 0.00 | 0.0 |
| | | 46 | 7.76 | 286.00 | 0.00 | 0.00 | 0.00 | 0.0 |
| | | 68 | 8.07 | 203.00 | 23.40 | 4.03 | 8.20 | 7.8 |
| 86 | Sphingomonas IFO 13937 | 18 | 5.09 | 233.00 | 0.00 | 0.00 | 0.00 | 0.0 |
| | | 46 | 5.13 | 260.00 | 23.00 | 0.00 | 0.00 | 7.7 |
| | | 68 | 5.13 | 199.00 | 0.00 | 0.00 | 0.00 | 0.0 |
| 87 | Sphingomonas IFO 15033 | 18 | 7.41 | 230.00 | 0.00 | 0.00 | 0.00 | 0.0 |
| | | 46 | 7.66 | 269.00 | 0.00 | 0.00 | 0.00 | 0.0 |
| | | 68 | 7.74 | 210.00 | 23.70 | 0.00 | 0.00 | 7.9 |
| 88 | Sphingomonas IFO 15098 | 18 | 8.30 | 232.00 | 0.00 | 0.00 | 0.00 | 0.0 |
| | | 46 | 8.33 | 270.00 | 13.70 | 0.00 | 0.00 | 4.6 |
| | | 68 | 8.41 | 239.00 | 0.00 | 0.00 | 0.00 | 0.0 | wherein

CHO: Cholesterol
25(OH)—CHO: 25-hydroxycholesterol
17,25(OH)—CHO: 17,25-dihydroxycholesterol
25,26(OH)—CHO: 25,26-dihydroxycholesterol Industrial Applicability According to the present invention, hydroxylated cholesterols including 25-hydroxycholesterol can be efficiently prepared, and 17,25-dihydroxycholesterol and 25,26-dihydroxycholesterol are provided as new hydroxylated cholesterols. These compounds are useful, for example, as intermediates for the preparation of vitamin D compounds and would be applicable in manufacturing industries for medicaments.

What is claimed is:

1. A method for preparing a hydroxylated cholesterol having the formula (II):

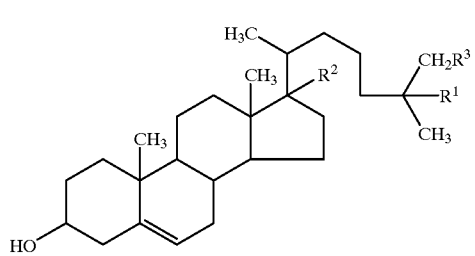

in which $R^1$ is a hydroxyl radical, and $R^2$ and $R^3$ are a hydroxyl radical and a hydrogen atom respectively, or a hydrogen atom and a hydroxyl radical respectively, by biological conversion of cholesterol having the formula (I):

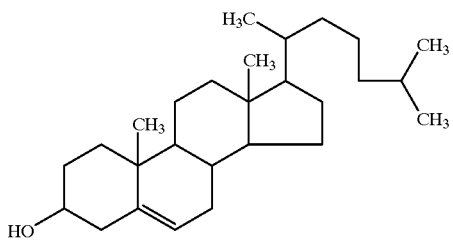

(I)

which method comprises:

(A) incubating cholesterol having the formula (I) with a strain of Amycolata or a preparation thereof which is able to biologically convert said cholesterol into the hydroxylated cholesterol having the formula (II), in an atmosphere containing oxygen, to produce an incubation-treated solution, in which (1) the hydroxylated cholesterol is either a compound having the formula (II) wherein $R^1$ and $R^2$ are a hydroxyl radical, and $R^3$ is a hydrogen atom, or a compound having the formula (II) wherein $R^1$ and $R^3$ are a hydroxyl radical, and $R^2$ is a hydrogen atom, and the strain of Amycolata is *Amycolata saturnea* FERM BP-5544, or (2) the hydroxylated cholesterol is a compound having the formula (II) wherein $R^1$ and $R^3$ are a hydroxyl radical, and $R^2$ is a hydrogen atom, and the strain of Amycolata is *Amycolata autotrophica* ATCC 33796; and (B) recovering the hydroxylated cholesterol from the incubation-treated solution.

2. The method according to claim 1, wherein incubation is carried out in the further presence of methylated cyclodextrins.

3. A method for preparing a dihydroxycholesterol having the formula (II-b):

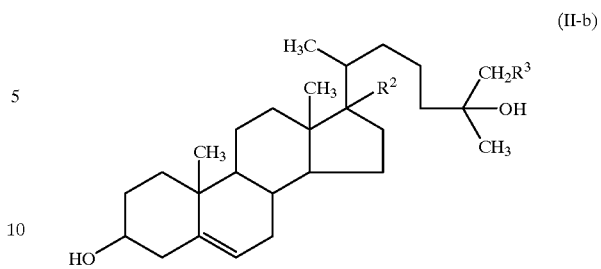

(II-b)

in which $R^2$ and $R^3$ are a hydroxyl radical and a hydrogen atom respectively, or a hydrogen atom and a hydroxyl radical respectively by biological conversion of 25-hydroxycholesterol having the formula (II-a):

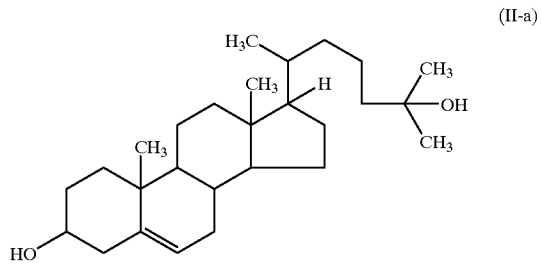

(II-a)

which method comprises:

(A) incubating 25-hydroxycholesterol having the formula (II-a) with *Amycolata saturnea* FERM BP-5544, or a preparation thereof which is able to biologically convert said 25-hydroxycholesterol into the dihydroxycholesterol having the formula (II-b), in an atmosphere containing oxygen, to produce an incubation-treated solution, and (B) recovering the dihydroxycholesterol from the incubation-treated solution.

4. The method according to claim 3, wherein incubation is carried out in the further presence of methylated cyclodextrins.

* * * * *